(12) United States Patent
Trammell

(10) Patent No.: US 7,560,614 B1
(45) Date of Patent: Jul. 14, 2009

(54) ROMAINE LETTUCE PYB 1595

(75) Inventor: Keith W. Trammell, Milwaukie, OR (US)

(73) Assignee: Pybas Vegetable Seed Co., Inc., Santa Maria, CA (US)

(*) Notice: Subject to any disclaimer, the term of this patent is extended or adjusted under 35 U.S.C. 154(b) by 0 days.

(21) Appl. No.: 12/112,941

(22) Filed: Apr. 30, 2008

(51) Int. Cl.
*A01H 1/00* (2006.01)
*A01H 5/00* (2006.01)
*A01H 5/10* (2006.01)

(52) U.S. Cl. .................. 800/305; 435/410; 800/260; 800/298

(58) Field of Classification Search ................ None
See application file for complete search history.

(56) References Cited

U.S. PATENT DOCUMENTS 7,321,078 B1 * 1/2008 Knerr et al. ............ 800/305

\* cited by examiner

*Primary Examiner*—David H Kruse
(74) *Attorney, Agent, or Firm*—Haynes and Boone, LLP

(57) ABSTRACT

A Romaine lettuce variety with improved resistance to corky root disease and lettuce dieback disease is presented. The seed of the lettuce is designated as PYB 1595, a representative sample of which has been deposited under ATCC Accession Number PTA-9179. PYB 1595 is a medium-dark green Romaine lettuce that combines the above disease resistance with Parris Island Cos (PIC) plant type. The invention is also directed to a method of making an F1 hybrid lettuce variety by crossing a plant grown from the seed of PYB 1595 with another plant and selecting a seed from said crossing.

10 Claims, No Drawings

ROMAINE LETTUCE PYB 1595

BACKGROUND

1. Field of Invention

This invention relates generally to the field of plant breeding and particularly to a variety of *Lactuca Sativa*.

2. Background

Lettuce is a popular crop that is enjoyed in many parts of the world raw or cooked. As the general population becomes more health-conscious, there is a continued increase of lettuce consumption and a demand for improved varieties. Desired characteristics of a lettuce include round head shape, uniformity, and ease of cultivation.

One of the factors that determine how easy a lettuce variety is to cultivate is its resistance to diseases. One of the common diseases that sabotage lettuce production is corky root, which typically appears as lesions on the root in the beginning. If left uncontrolled, plants infected with corky root will be completely destroyed. In some parts of the country, corky root is known to destroy as much as 50% of the crop. While fumigants such as dazomet, metam sodium and methyl bromide+chloropicrin are known to be effective for controlling corky root, the application of these materials on a commercial scale is undesirably costly.

Another disease that could destroy lettuce is the lettuce dieback disease. Lettuce dieback disease, which is a soil-borne disease caused by the Tomato Bush Stunt Virus (TBSV) and Lettuce Necrotic Stunt Virus (LNSV), can severely compromise lettuce production.

A lettuce variety that is less susceptible to diseases and relatively easy to cultivate on a large scale is desired.

SUMMARY

The invention is directed to a lettuce variety with improved resistance to corky root disease and lettuce dieback disease. The seed of the lettuce is designated as PYB 1595, a representative sample of which has been deposited under ATCC Accession Number PTA-9179. PYB 1595 is a medium-dark green Romaine lettuce with corky root resistance and lettuce dieback resistance.

The Romaine lettuce of the invention, named PYB 1595, is a medium-dark green Romaine lettuce. PYB 1595 is desirable for its resistance to the corky root disease and the lettuce dieback disease. In fact, PYB 1595 is the first Romaine variety to combine these two diseases resistance with the desirable Parris Island Cos (PIC) plant type.

Other features and aspects of the invention will become apparent from the following detailed description, taken in conjunction with the accompanying drawings which illustrate, by way of example, the features in accordance with embodiments of the invention. The summary is not intended to limit the scope of the invention, which is defined solely by the claims.

DETAILED DESCRIPTION

Romaine lettuce, also known as *Lactuca sativa* L. var. *longifolia* Lam, develops in an upright open or upright compact growing habit with coarse textured leaves. The leaves are longer than they are wide, and cup together to form an elongated loose head. Leaf margins are often entire or undulated, rarely frilled. Leaves range in color from light green to dark green with a heavy midrib. Inner heart leaves are smaller and are generally lighter in color than the outer leaves. Romaine lettuces are often used in salads, and "Romaine hearts" may be used in various dishes other than salads.

The Romaine lettuce of the invention, named PYB 1595, is a medium-dark green Romaine lettuce. PYB 1595 is desirable for its resistance to the corky root disease and the lettuce dieback disease. In fact, PYB 1595 is the first Romaine variety to combine these two diseases resistance with the desirable Paris Island Cos (PIC) plant type.

Breeding History

The Romaine lettuce PYB 1595 was derived from a cross between (Bautista×Darkland Cos)×Skyway in the summer of 2000. PYB 1595 was developed via the well-known pedigree breeding method. The pedigree breeding method is a breeding technique in which the pedigrees of successive generations are recorded and by which successive generations of segregating individual plants are selected following an initial cross. The female in the cross, (Bautista×Darkland Cos), was a corky-root resistant, advanced breeding line. Darkland is a very dark green Romaine variety without any disease resistance introduced by Central Valley Seed Company, and Bautista is a dark green, corky-root resistant Romaine variety owned by Seminis Seed Company. Bautista was derived from the cross Paris Island Cos×Tall Guzmaine. The male in the cross, Skyway, is owned by Pybas Vegetable Seed Company and is both corky-root resistant and lettuce dieback-resistant. Skyway is a baby-leaf Romaine type derived from the cross Bautista×El Dorado. El Dorado is a small heading iceberg lettuce variety that carries resistance to the lettuce dieback disease.

In the summer of 2001, the F1 generation seed of the cross (Bautista×Darkland Cos)×Skyway was grown. Then, in the spring of 2002, next generation was planted in trials in Santa Maria, Calif. The F2 generation was quite variable, segregating plants with leaves with a tinge of red pigment and Romaine types which varied considerably in their shapes, sizes, and their shades of green. There were a few promising individual Romaine type without the red pigmentation. Seven of these more interesting single plants were selected.

In the fall of 2002, the F3 seed was harvested from these selected seven single plants. In July of 2003, the F3 seeds were planted to a Romaine lettuce trial near Guadalupe, Calif. Four selections were made from the best of the F3 plots. This plot was entirely free of any red pigment, and most of the plants approximated the desirable standard PIC type, though they were darker green than PIC. F4 seed from these four selections were harvested late in 2003.

In 2004, remnant seed of the same F3 was planted to a field in Oceano, Calif. which is known to be infested with the lettuce dieback disease. Also in 2004, the F4s were planted to a trial in Santa Maria and in the commercial seed production area near Buttonwillow, Calif. in the San Joaquin Valley.

F5 seed was saved on five slow-bolting plants in Buttonwillow from the F4 plot judged to be the best in the Santa Maria trial. From the Oceano trial, it was observed that the line was segregating for resistance to lettuce dieback in the F3 generation.

In April of 2005, the F5 lines were planted to a trial near Guadalupe in a field infested with corky root disease. One of the lines appeared especially promising. By pulling and examining the root systems of several plants, it was found to be resistant to corky root when compared to a susceptible check. It also had an excellent PIC plant type, short cores, and was slow to develop any tip burn, a disorder that appears in lettuce at the time of harvest in which small brown spots appear on the margins of the leaves. It segregated for green color, varying from medium to very dark green. Three ideal medium to dark green plants were selected. F6 seed was harvested from them in late summer, 2005.

In May of 2006, three F6 lines were planted in a trial near Los Alamos, Calif. and in Buttonwillow, Calif. The trial field in Los Alamos had sufficient corky root to be able to confirm the resistance of the lines. Two of the three lines continued to segregate for the intensity of green color. The third was a uniform medium-dark green. For this F6 in Buttonwillow, the seed was bulked (F7B). The line was given the experimental designation PYB 1595.

The F7B seed lot was used for trialing purposes late in 2006 and in 2007, and was used as stock seed for a large-scale increase in Buttonwillow in 2007. In July of 2007, F7B seeds were sowed on the same site in Oceano as used in 2004, and the line was found to be resistant to lettuce dieback.

| Characteristics of PYB 1595 | | |
|---|---|---|
| Characteristic | SKYWAY | PYB 1595 |
| Head Weight (grams) | 679 | 710 |
| Core Diameter (cm) | 37.5 | 39 |
| Reaction to Corky Root | RESISTANT | RESISTANT |
| Reaction to Lettuce Dieback Disease | RESISTANT | RESISTANT |

The table above compares PYB 1595 with Skyway, which is a commercial variety that is similar to PYB 1595.

While the invention has been described in terms of illustration and examples for purposes of clarity and understanding, the description is not intended to be exhaustive or to limit the invention to the precise form disclosed. It should be understood that the invention can be practiced with modification and alteration do not depart from the spirit and scope of the invention as defined by the appended claims.

What is claimed is:

1. A lettuce seed designated as PYB 1595, a representative sample of which has been deposited under ATCC Accession Number PTA-9179.

2. A lettuce plant produced by growing the seed of claim 1.

3. A plant part from the plant of claim 2.

4. A lettuce plant having all of the physiological and morphological characteristics of the lettuce plant of claim 2.

5. A plant part from the plant of claim 4.

6. Pollen of the plant of claim 2.

7. An ovule of the plant of claim 2.

8. A tissue culture of the plant of claim 2.

9. A method of producing lettuce seeds comprising crossing the plant of claim 2 with another lettuce plant and harvesting a seed therefrom.

10. A method of making an F1 hybrid lettuce variety comprising:

crossing a lettuce plant with a plant grown from the seed of claim 1; and selecting a seed from said crossing.

* * * * *